United States Patent [19]

Arena

[11] 4,380,679

[45] Apr. 19, 1983

[54] HYDROGENATION OF SACCHARIDES

[75] Inventor: Blaise J. Arena, Des Plaines, Ill.

[73] Assignee: UOP Inc., Des Plaines, Ill.

[21] Appl. No.: 367,494

[22] Filed: Apr. 12, 1982

[51] Int. Cl.$^3$ .............................................. C07C 31/26
[52] U.S. Cl. .................................................. 568/863
[58] Field of Search ........................................ 568/863

[56] References Cited

U.S. PATENT DOCUMENTS

| | | | |
|---|---|---|---|
| 2,642,462 | 6/1953 | Kasehager | 568/863 |
| 2,868,847 | 1/1959 | Boyers | 568/863 |
| 3,651,386 | 3/1972 | Youtsey et al. | 317/237 |
| 3,784,408 | 1/1974 | Jaffe et al. | 568/863 |
| 3,935,284 | 1/1976 | Kruce | 568/863 |
| 4,319,058 | 3/1982 | Kulprathipanja et al. | 568/917 |
| 4,329,260 | 5/1982 | Lester et al. | 252/463 |

Primary Examiner—Joseph E. Evans
Attorney, Agent, or Firm—James R. Hoatson, Jr.; Raymond H. Nelson; William H. Page, II

[57] ABSTRACT

Saccharides such as glucose, fructose, starch, etc. may be hydrogenated by treatment with hydrogen in the presence of a catalyst which comprises a metal of Group VIII of the Periodic Table composited on a support comprising a carbonaceous pyropolymer possessing recurring units containing at least carbon and hydrogen atoms at a temperature in the range of from about 90° to about 150° C. and a pressure in the range of from about 500 to about 3000 psi to obtain polyols. In such a manner, glucose may be hydrogenated to sorbitol and mannitol.

13 Claims, No Drawings

HYDROGENATION OF SACCHARIDES

BACKGROUND OF THE INVENTION

Saccharides are chemical compounds which are found in many naturally-occurring substances. Included among these compounds are various sugars and carbohydrates. Among the sugars are found monosaccharides, disaccharides and polysaccharides. While the sugars themselves, including monosaccharides such as glucose, mannose, galactose, talose, fructose, allose, altrose, idose, gulose, xylose, lyxose, ribose, arabinose, threose, erythrose, etc., disaccharides such as maltose, cellobiose, sucrose, lactose, etc., or polysaccharides such as starch, cellulose, etc., are important chemical compounds, the hydrogenated products which may be obtained by hydrogenating said compounds are also important. For example, sorbitol, which may be obtained by hydrogenating glucose, will find a wide variety of uses such as in the manufacture of explosives, use in the synthesis of ascorbic acid, etc. or in solution form as an additive for cosmetic creams and lotions and toothpaste, tobacco, etc., as a bodying agent for paper, textiles, and liquid pharmaceuticals such as syrups, elixirs, etc., in the synthesis of resins, surface active agents, varnishes, etc. Likewise, mannitol, which may be obtained from fructose, will find various uses such as a base for tableting, as an ingredient in electrolytic condensers, as a basis of dietetic sweets, etc.

In hydrogenating these saccharides, it is an advantage to conduct the hydrogenation in an aqueous media due to the solubility of the saccharides in water with a concurrent generally insolubility in most organic solvents. The hydrogenation of these saccharides is usually accomplished using a metal hydrogenation catalyst, preferably one in which the metal is dispersed on a support. However, limitations on such metal catalyst composites have been found due to the lack of hydrothermal stability of the commonly used supports. This lack of stability exhibits disadvantages in that the lifetime of the catalyst is generally limited as well as providing the necessity for subsequent operation steps to remove any extraneous material which may be present in the reaction product due to the dissolved support material contained therein. This is particularly true when using traditional support materials such as the various aluminas and silica.

As will hereinafter be shown in greater detail, it has now been discovered that saccharides may be successfully hydrogenated utilizing a catalyst in which the catalytically active metal is composited on a particular type of support, said support being hydrothermally stable to the reaction conditions employed for the hydrogenation process.

BRIEF SUMMARY OF THE INVENTION

This invention relates to a process for the hydrogenation of saccharides. More particularly, the invention is concerned with a process for the hydrogenation of saccharides utilizing, as a hydrogenation catalyst therefor, a hydrogenation metal composited on a particular type of support, the support being more particularly hereinafter described.

It is therefore an object of this invention to provide a process for the hydrogenation of saccharides.

A further object of this invention is to provide a process for the catalytic hydrogenation of saccharides using a hydrothermally stable catalyst.

In one aspect, an embodiment of this invention resides in a process for the hydrogenation of a saccharide which comprises treating said saccharide with hydrogen at hydrogenation conditions in the presence of a catalyst comprising a metal of Group VIII of the Periodic Table composited on a support comprising a carbonaceous pyropolymer possessing recurring units containing at least carbon and hydrogen atoms, and recovering the resultant hydrogenated saccharide.

A specific embodiment of this invention is found in a process for the hydrogenation of glucose which comprises treating said glucose with hydrogen at a temperature in the range of from about 90° to about 150° C. and a pressure in the range of from about 500 to about 3000 pounds per square inch (psi) in the presence of a hydrogenation catalyst comprising ruthenium composited on a support comprising a carbonaceous pyropolymer possessing recurring units containing at least carbon and hydrogen atoms, said support comprising an integral shaped replication of a particle aggregate, and recovering the resultant sorbitol.

Other objects and embodiments may be found in the following further detailed description of the present invention.

DETAILED DESCRIPTION OF THE INVENTION

As hereinbefore set forth, the present invention is concerned with a process for the hydrogenation of saccharides, the saccharides or carbohydrates as they may also be termed, can be hydrolyzed to the corresponding polyols. Among the saccharides which may be hydrogenated to the corresponding polyols to form important articles of commerce are monosaccharides such as glucose, mannose, and fructose, disaccharides such as maltose, and polysaccharides such as starch or cellulose due to their greater availability. The hydrogenation of the saccharides is effected, according to the process of this invention, by treating the saccharides with hydrogen in the presence of certain catalytic compositions of matter at treatment conditions. In accordance with the process of this invention, the hydrogenation of the saccharides is accomplished at reaction conditions which include a temperature in the range of from about 90° to about 150° C. or more, while employing pressures which may range from about 500 to about 3000 psi or more. In the preferred embodiment of the invention, the pressures are afforded by hydrogen, although it is also contemplated within the scope of this invention that the amount of hydrogen which is employed may afford only a partial pressure, the remainder of the desired operating pressure being afforded by the introduction of an inert gas such as nitrogen, argon, helium, etc. into the reaction zone. The hydrogenation process may be effected over a relatively wide time span, depending upon the particular temperature and pressure which is employed, the duration of the hydrogenation usually being from about 0.5 up to about 4 hours or more.

The hydrogenation of the saccharides of the type hereinbefore set forth in greater detail is effected in the presence of a catalyst comprising a metal of Group VIII of the Periodic Table deposited on a particular support. Examples of metals of Group VIII which may be employed will include cobalt, iron, nickel, ruthenium, rhodium, osmium, iridium, palladium and platinum, etc. The support upon which the aforesaid metals are composited will comprise a carbonaceous pyropolymer possessing recurring units containing at least carbon and hydrogen atoms composited on a high surface area inorganic oxide or a carbonaceous pyropolymer possessing recurring units containing at least carbon and hydrogen atoms which is an integral shaped replication of a particle aggregate.

The supports which may be employed may be prepared by treating an inorganic support which will include high surface area refractory oxides such as alumina in various forms including gamma-alumina, eta-alumina, theta-alumina, or mixtures of inorganic refractory oxides such as zeolites, silica-alumina, silica-zirconia, zirconia-titania, zirconia-alumina, etc. The shape of the inorganic substrate material may comprise any type of structure or shape such as spheres, plates, pellets, rods, fibers, monoliths, etc., the particular form or shape of the substrate material being obtained by any method known in the art such as marumerizing, pelletizing, modulizing, etc. The inorganic support material will usually possess a surface area of from about 1 to about 500 square meters per gram as well as a pore structure which includes both micropores and macropores.

In one method of preparing the composite, the inorganic support such as a refractory oxide is heated to a temperature of from about 400° to about 1200° C. in a reducing atmosphere containing an organic pyrolyzable compound. The organic pyropolymer precursors most commonly and preferably used for the purposes of this invention are members of the group consisting of aliphatic hydrocarbons, aliphatic halogen derivatives, aliphatic oxygen derivatives, aliphatic sulfur derivatives, aliphatic nitrogen derivatives, organometallic compounds, alicyclic compounds, aromatic compounds, and heterocyclic compounds. Of the aliphatic hydrocarbons, the more common classes which may be utilized to perform this invention are alkanes, alkenes, alkynes and alkadienes. Ethane, propane, butane and pentane are among the alkanes which may be successfully used in the performance of this invention. Similarly, alkenes which suffice include ethene, propene, 1-butene, 2-butene and 1-pentene. Alkynes which may be successfully used include ethyne, propyne, 1-butyne, 2-butyne, 1-pentyne, and 1-hexyne. 1,3-Butadiene and isoprene are included among the alkadienes which may be utilized. Among the aliphatic halogen derivatives which suffice for the purposes of this invention are monohaloalkane subgroup, chloromethane, bromoethane, 1-iodopropane, and 1-chlorobutane may be used. Polyhaloalkanes such as carbon tetrachloride, chloroform, 1,2-dichloroethane and 1,2-dichlorobutane may also be utilized. One unsaturated halo compound which may be utilized is chloroprene.

The aliphatic oxygen derivatives appropriate for use in this invention include the classes of alcohols, ethers, halohydrides and alkene oxides, saturated aldehydes and ketones, unsaturated aldehydes and ketones, ketenes, acids, esters, salts and carbohydrates. Various alcohols which may be utilized include ethanol, 2-butanol, 1-propanol, glycol, (e.g., 1,3-propanediol), and glycerol. Ethers utilized include ethyl ether and isopropyl ether. Appropriate halohydrins and alkene oxides include ethylene chlorohydrin, propylene chlorohydrin, ethylene oxide, and propylene oxide. Suitable saturated aldehydes and ketones include formaldehyde, acetaldehyde, acetone and ethyl methyl ketone. Unsaturated aldehydes and ketones which may be used include propenol, trans-2-butenal and butenone. Ketene has also been successfully used as an organic pyrolyzable substance. Likewise, formic acid, acetic acid, oxalic acid, acrylic acid, chloroethanoic acid, formic anhydride and formyl chloride may also be utilized. Ethers such as methyl formate, ethyl formate and ethyl acetate may also be used. Salts such as sodium formate, potassium acetate and calcium propionate may be utilized as may a variety of carbohydrates. The broad classification of aliphatic sulfur derivatives may be broken down into the subclasses of alkanethiols, alkylthioalkanes, sulfonic acids, and alkyl sulfates and alkyl metallic sulfates. Suitable among the alkanethiols are ethyl mercaptan and n-propyl mercaptan. Among the alkylthioalkanes usable are the thioethers, alkyl sulfides, methyl sulfide, ethyl sulfide and methyl propyl sulfide. Ethyl sulfonic acid and n-propyl sulfonic acid are sulfonic acids which may also be successfully used. Ethyl sulfate and sodium laurel sulfate are also appropriate for use.

The broad class of aliphatic nitrogen derivatives may be broken down into the subclasses of nitroalkanes, amides, amines, nitriles and carbylamines. Nitroethane and 1-nitropropane are exemplary of suitable nitroalkanes while acetamide and propioamide are among the appropriate amides. Amines such as dimethylamine and ethylmethylamine, nitriles such as acetonitrile and propionitrile, and carbylamines such as ethyl isocyanide may also be used for the organic pyrolyzable substance of this invention. Organometallic compounds such as tetraisopropyl titanate, tetrabutyl titanate and 2-ethylhexyl titanate may also be used.

Particularly appropriate and preferred for use as the organopyrolyzable substance of this invention are the alicyclic compounds. Foremost among these are cyclohexane and cyclohexene. Aromatic compounds include the subclasses of hydrocarbons, halogen compounds, oxygen derivatives, ethers, aldehydes, ketones, quinones; aromatic acids, aromatic sulfur derivatives, and aromatic nitrogen compounds may also be utilized. Among the many suitable hydrocarbons, benzene, naphthalene, anthracene, and toluene were successfully utilized. Benzyl chloride and benzal chloride are appropriate halogen compounds, while phenol, o-cresol, benzyl alcohol and hydroquinone are among the suitable derivatives. Ethers such as anisole and phenetole and aldehydes, ketones, and quinones, such as benzaldehyde, acetophenone, benzophenone, benzoquinone and anthraquinone may also be used. Aromatic acids such as benzoic acid, phenylacetic acid, and hydrocinnamic acid may be utilized while the aromatic sulfur derivative of benzene sulfonic acid will also serve successfully. The aromatic nitrogen compounds of nitrobenzene, 1-nitronaphthalene, aminobenzene and 2-amine toluene may also be successfully used as the organic pyrolyzable substance of this invention. Among the heterocyclic compounds, five member ring compounds such as furan, proline, coumarone, thionaphthene, indole, indigo, and carbazole may be successfully utilized. Six member ring compounds such as pyran, coumarin and acridine may also be utilized.

As can be seen, an extremely wide latitude can be exercised in the selection of the organic pyrolyzable substance, since virtually any organic material that can be vaporized, decomposed and polymerized on the refractory oxide by heating will suffice. The resultant carbonaceous pyropolymer will possess recurring units containing at least carbon and hydrogen atoms; however, depending upon the pyropolymer precursor which has been selected, the pyropolymer may also contain other atoms such as nitrogen, oxygen, sulfur, or metals such as phosphorus, etc.

In another emodiment, the composite may be prepared by impregnating the refractory inorganic oxide with a solution of a carbohydrate material such as dextrose, sucrose, fructose, starch, etc., and thereafter drying the impregnated support. After drying, the impregnated support is then subjected to pyrolysis temperatures in the range hereinbefore set forth whereby a carbonaceous pyropolymer similar in nature to those hereinbefore described is formed in at least a monolayer on the surface of the refractory inorganic oxide support.

In the event that the catalyst support which is employed in the process of this invention comprises the integral shaped replication of particle aggregates, the composite thus prepared according to the above description will be further treated by chemically leaching the inorganic support from the carbonaceous pyropolymer. The amount of carbonaceous pyropolymer which has been deposited on the surface of the support will have been sufficient to duplicate the physical shape and dimension of the substrate as well as a substantial portion of the pore structure thereof. The leaching is effected by treating said composite with either an acid or a base, thereby forming a high surface area carbonaceous pyropolymer support which is a shaped replication of the original inorganic support. The leaching of the base material of the type hereinbefore set forth may be effected over a wide range of temperatures, said range being from about ambient (20°-25° C.) up to about 250° C. or more for a period of time which may range from less than 1 up to about 72 hours or more. It is to be understood that the operating parameters of the leaching step will vary over a wide range and will be dependent upon a combination of time, temperature, strength of the leaching solution, etc. Examples of acids or bases which may be utilized to leach out the base material include inorganic acids such as phosphoric acid, sulfuric acid, nitric acid, hydrochloric acid, etc., organic acids such as methyl sulfonic acid, ethyl sulfonic acid, propyl sulfonic acid, toluene sulfonic acid, etc., strong bases such as sodium hydroxide, potassium hydroxide, lithium hydroxide, rubidium hydroxide, cesium hydroxide, etc. It is to be understood that the aforementioned leaching materials are only representative of the class of compounds which may be used and that any chemical which is capable of removing the refractory inorganic oxide while retaining the high surface area of the carbonaceous pyropolymer may be used. The resulting shaped replication of particle aggregates thus prepared will possess a high surface area, a desired pore volume as well as a high crush strength, thereby enabling the shaped replication of a carbonaceous pyropolymer possessing recurring units containing at least carbon and hydrogen atoms to be utilized as a support for the aforementioned metals of Group VIII of the Periodic Table.

The deposition of the metal of Group VIII of the Periodic Table on the aforementioned supports may be effected by treating the carbonaceous pyropolymer structures with an aqueous or organic solution of the desired metal in an amount sufficient to deposit the catalytically active metal on the surface of the carbonaceous pyropolymer support in an amount ranging from about 0.1 to about 30% by weight. The solution which is utilized to impregnate the carbonaceous pyropolymer structure is preferably aqueous in nature, some specific examples of these aqueous solutions being chloroplatinic acid, chloroplatinous acid, bromoplatinous acid, sodium platinate, potassium platinate, platinic chloride, palladium chloride, palladium sulfate, diaminepalladium (II) hydroxide, tetraminepalladium (II) chloride, chloropalladinic acid, chloropalladinous acid, ruthenium tetrachloride, osmium trichloride, nickel chloride, nickel sulfate, nickel nitrate, etc. It is to be understood that the aforementioned compounds are only representative of the type of compounds which may be used to impregnate the support and that the present invention is not necessarily limited thereto. After impregnation of the structure, the solvent is removed by heating to a temperature in the range of from about 100° to about 400° C., the temperature being that which is sufficient to evaporate said solvent and leave the metal impregnated on the surface of the carbonaceous pyropolymer structure. Thereafter, the structure may then be dried at elevated temperatures ranging from about 100° to about 600° C. for a period of time ranging from about 2 to about 6 hours or more. Thereafter, the metal impregnated carbonaceous pyropolymer structure is then subjected to a reducing step in the presence of a reducing atmosphere or medium such as hydrogen at elevated temperatures of from about 200° to about 600° C. or more for a period of time ranging from about 0.5 to about 4 hours or more whereby the metallic compound is reduced to the metal in the form of particles.

The process of hydrogenating a saccharide in the presence of the hereinbefore described catalytic composition of matter may be effected in any suitable manner and may comprise either a batch or continuous type of operation. For example, when a batch type operation is employed, a quantity of the saccharide and the catalyst is placed in an appropriate apparatus which may comprise a pressure-resistant vessel such as an autoclave of the mixing or rotating type. The apparatus is sealed and hydrogen is pressured in until the desired initial operating pressure is reached. Following this, the apparatus and contents therein are heated to the desired operating temperature and, if a higher operating pressure is desired, additional hydrogen is pressured in. The reaction is allowed to proceed for a predetermined period of time which, as hereinbefore set forth may be in the range of from about 0.5 up to about 4 hours or more in duration. At the end of the predetermined residence time, heating is discontinued and the apparatus is allowed to cool to room temperature. Upon reaching ambient temperature, any excess pressure is discharged and the apparatus is opened. The reaction mixture is recovered, separated from the catalyst by conventional means such as filtration, centrifugation, etc. and then subjected to other separation means such as liquid chromatography whereby the desired polyols are separated from any unreacted starting materials and recovered.

It is also contemplated within the scope of this invention that the hydrogenation process may be effected in a continuous manner of operation. When such a type of operation is employed, the starting material comprising the saccharide is continuously charged to a pressure-resistant apparatus which is maintained at the proper operating conditions of temperature and pressure, said pressure being afforded by hydrogen or a mixture of hydrogen and an inert gas of the type previously described. The saccharide will contact the hydrogenation catalyst which is contained in the reactor for a predetermined period of time following which the reactor effluent is continuously withdrawn and subjected to separation means such as crystallization, etc. whereby the desired polyols are separated from unreacted saccharides and recovered, the saccharides being recycled back to the reactor to form a portion of the feedstock.

Inasmuch as the catalyst which is employed for the hydrogenation of the saccharides to polyols is solid in nature, it is contemplated that various types of continuous processes may be employed. For example, the catalyst may be positioned in the reactor in a fixed bed and the feedstock comprising the polysaccharide solution may be passed over the fixed catalyst bed in either an upward or downward flow. Another type of operation which may be employed comprises the moving bed process in which the polysaccharide is contacted with a moving bed of catalyst in flows which are either concurrent or countercurrent to each other. Yet a third type of operation which may be used comprises the slurry type of operation in which the hydrogenated catalyst is carried into the reactor as a slurry in the saccharide solution.

The following examples are given for purposes of illustrating the process of the present invention. However, it is to be understood that these examples are given merely for purposes of illustration and that the present invention is not necessarily limited thereto.

EXAMPLE I

A solution comprising 0.8 gram of ruthenium chloride dissolved in 40 ml of deionized water was added to 6.0 grams of a carbonaceous pyropolymer possessing recurring units containing at least carbon and hydrogen atoms, which were a shaped replica of spheres, and mixed for 0.5 hours. The solution was then evaporated by steam heating, leaving the carbonaceous pyropolymer spheres impregnated with ruthenium chloride. The impregnated spheres were calcined in a stream of nitrogen for a period of 2.7 hours at a temperature of 400° C. followed by a reduction in a stream of hydrogen for three hours at 400° C.

The catalyst composition which comprised 5% ruthenium on the carbonaceous pyropolymer spheres was placed in a 300 cc autoclave containing stirring apparatus. The autoclave was charged with 60 ml of a 50% aqueous glucose solution and the autoclave was sealed. Hydrogen was pressed in until an initial operating pressure of 700 psi was reached and the autoclave was then heated to a temperature of 120° C. Upon reaching the desired operating temperature, excess $H_2$ pressure was vented to 700 psi. The autoclave was maintained at this temperature and pressure for a period of 5 hours during which time the reaction mixture was continuously agitated by use of the stirring means. At the end of the 5 hour period, heating was discontinued and the system was allowed to return to ambient temperature. The excess pressure was vented, the autoclave was opened and the reaction solution was removed. A sample was submitted for high pressure liquid chromatography analysis. The analysis disclosed that there had been a 99.0% conversion of the glucose with a 91.3% selectivity to sorbitol and 3.1% mannitol.

EXAMPLE II

In this example, a catalyst similar in nature to that hereinbefore set forth was prepared by treating 6.0 grams of carbonaceous pyropolymer spheres, which had been prepared according to the method set forth in the foregoing specification, with a solution of nickel nitrate and chloroplatinic acid in an amount sufficient to deposit 25% by weight of nickel and 5% by weight of platinum on the spheres after calcination in the presence of nitrogen at 400° C. and reduction in the presence of hydrogen at 400° C. As in the preceding example, 2 grams of this catalyst, along with 60 ml of a 50% aqueous glucose solution, were placed in an autoclave provided with stirring means which was thereafter sealed. Hydrogen was pressed in until an initial operating pressure of 700 psi was reached and the autoclave was heated to a temperature of 120° C., following which the reaction was allowed to proceed for a period of 5 hours with stirring at these operating conditions of temperature and pressure. At the end of the 5 hour period, heating was discontinued, the autoclave was allowed to return to ambient temperature and, after reaching this temperature, the excess pressure was discharged. The autoclave was opened and after recovery of the reaction mixture, analysis by means of high pressure liquid chromatography determined that there had been a 99.2% conversion of the glucose with a 92.8% selectivity to sorbitol and 1.9% to mannitol.

EXAMPLE III

A catalyst was prepared by impregnating 6 grams of a base, which was prepared by impregnating a carbonaceous pyropolymer comprising recurring units containing at least carbon and hydrogen atoms composited on a gamma-alumina support, the base also being prepared in a manner previously disclosed in the foregoing specification, with 0.8 grams of ruthenium chloride dissolved in 40 cc of deionized water. After allowing the impregnation to proceed for a period of 0.5 hours, the solution was evaporated by steam heating and the resulting impregnated spheres were calcined in flowing nitrogen for 2.7 hours at 400° C. The calcined spheres were then reduced in flowing hydrogen for a period of 3 hours at 400° C. and 2 grams of this catalyst were used. The catalyst and 60 ml of a 50% aqueous glucose solution were placed in an autoclave which was sealed, pressured to 700 psi with hydrogen, and heated to 120° C. The reaction mixture was stirred for a period of 5 hours while maintaining the aforementioned operating conditions of temperature and pressure. At the end of the 5 hour period, heating was discontinued and after the autoclave had reached ambient temperature, the excess pressure was discharged and the autoclave was opened. The reaction mixture was recovered and analyzed by means of high pressure liquid chromatography. This analysis disclosed that there had been a 75% conversion of the glucose with a 56.2% selectivity to sorbitol and 3.5% to mannitol.

EXAMPLE IV

In this example, the catalyst, which was used for the hydrogenation of glucose and which was prepared in a manner similar to that hereinbefore set forth in the above examples, comprised 30% nickel composited on carbonaceous pyropolymer spheres. The reaction mixture which comprised 60 ml of a 50% aqueous glucose solution and 2 grams of this catalyst were treated in an autoclave for a period of 5 hours at a temperature of 120° C. and a pressure of 700 psi of hydrogen. Analysis of the product which was recovered from this test by means of high pressure liquid chromatography disclosed a 96% conversion of the glucose with a 98.5% selectivity to sorbitol and 0.3% selectivity to mannitol.

EXAMPLE V

In this example, further experiments were performed using catalysts comprising 5% of platinum, 5% of palladium and 5% of rhodium composited on carbonaceous pyropolymer spheres similar in nature to the spheres used in Example I above. These catalysts were used in the hydrogenation of a 50% aqueous glucose solution under reaction conditions similar to those hereinbefore set forth. After treatment at a temperature of 120° C. and a hydrogen pressure of 700 psi for a period of 5 hours, the analysis of the reaction product showed that there had been a 54.5% conversion of the glucose when using the platinum catalyst, a 38.0% conversion of the glucose when using the palladium catalyst and a 25.0% conversion of the glucose when using the rhodium catalyst.

EXAMPLE VI

To illustrate greater activity of the catalyst of the present invention, that is, a metal of Group VIII of the Periodic Table composited on a carbonaceous pyropolymer possessing recurring units containing at least carbon and hydrogen atoms, a comparative example was performed in which the catalyst utilized from the hydrogenation of glucose comprises a 5% ruthenium composited on carbon. Using identical reaction conditions to those described in the above examples, analysis of the product which was recovered from the hydrogenation showed there had been a 24.0% conversion of the glucose with only a 12.0% selectivity to sorbitol. This is in marked contrast to the conversions of 75% and above when using ruthenium, nickel, or a mixture of nickel and platinum composited on a carbonaceous pyropolymer sphere or a sphere comprising a carbonaceous pyropolymer composited on an alumina support.

EXAMPLE VII

In addition to the greater activities exhibited by the catalyst described in the present specification in the hydrogenation of saccharides to polyols, another advantage which accrues to the use of these catalysts lies in the hydrothermal stability of said catalyst. To illustrate this hydrothermal stability, 2.7 grams of a carbonaceous pyropolymer possessing recurring units containing at least carbon and hydrogen atoms composited on a high surface area alumina support, was leached with 50 ml of a 50% aqueous sorbitol solution which was placed in an autoclave. The autoclave was pressured to 2400 psi with hydrogen, heated to a temperature of 130° C. and agitated for a period of 24 hours. The resulting mixture, after discontinuance of heating, returned to ambient temperature and vented of the excess pressure, was recovered, filtered, and analyzed for dissolved aluminum. Only 1.9 ppm of soluble aluminum was recovered.

In contrast to this, an identical test was performed using 2.5 grams of gamma-alumina which was the alumina used to prepare the carbonaceous pyropolymer-coated catalyst. After treatment of the 2.5 grams of alumina with 50 ml of a 50% sorbitol solution at a temperature of 130° C. and a pressure of 2400 psi of hydrogen for a period of 24 hours, the resulting mixture was recovered. The mixture was filtered and analyzed for dissolved aluminum. In this case, 129 ppm of soluble aluminum was recovered. It is thus apparent from a comparison of the two bases that the carbonaceous pyropolymer coating was effective in preventing the dissolution of aluminum and thus, it is readily apparent that the carbonaceous pyropolymer-coated base will exhibit a much greater hydrothermal stability than the uncoated alumina.

EXAMPLE VIII

As a further illustration of the advantages of utilizing the type A catalyst hereinbefore described for the hydrogenation of saccharides, a continuous type of operation was tested. A catalyst similar in nature to that described in Example I above was prepared and 100 cc of this 5% ruthenium on carbonaceous pyropolymer spheres was placed in a reaction vessel. The temperature of the vessel was maintained at 120° C. while a feedstock comprising a 50% aqueous glucose solution was continuously charged thereto. The glucose solution was charged at a liquid hourly space velocity of 0.25 while hydrogen was pressed in in an amount so that the hydrogen-to-glucose ratio was 10:1 and the pressure was 700 psi. The reactor effluent, which was continuously recovered from the reactor, was analyzed by means of high pressure liquid chromatography, said analysis disclosing that there had been a 98% conversion of the glucose with a 96% selectivity to sorbitol.

A repeat of the above experiment using the same type of catalyst and a feed comprising 50% aqueous glucose solution with a pressure of 2000 psi of hydrogen resulted in a 98% conversion of glucose with a 98% selectivity to sorbitol.

I claim as my invention:

1. A process for the hydrogenation of a saccharide which comprises treating said saccharide with hydrogen at hydrogenation conditions in the presence of a catalyst comprising a metal of Group VIII of the Periodic Table composited on a support comprising a carbonaceous pyropolymer possessing recurring units containing at least carbon and hydrogen atoms, and recovering the resultant hydrogenated saccharide.

2. The process as set forth in claim 1 in which said hydrogenation conditions included a temperature in the range of from about 90° to about 150° C. and a pressure in the range of from about 500 to about 3000 pounds per square inch.

3. The process as set forth in claim 1 in which said carbonaceous pyropolymer comprises an integral shaped replication of a particle aggregate.

4. The process as set forth in claim 1 in which said carbonaceous pyropolymer is composited on a high surface area inorganic oxide.

5. The process as set forth in claim 4 in which said high surface area inorganic oxide is an alumina.

6. The process as set forth in claim 5 in which said alumina is gamma-alumina.

7. The process as set forth in claim 1 in which said metal of Group VIII of the Periodic Table is ruthenium.

8. The process as set forth in claim 1 in which said metal of Group VIII of the Periodic Table is nickel.

9. The process as set forth in claim 1 in which said metal of Group VIII of the Periodic Table is platinum.

10. The process as set forth in claim 1 in which said metal of Group VIII of the Periodic Table is palladium.

11. The process as set forth in claim 1 in which said saccharide is glucose and said hydrogenated saccharide is sorbitol.

12. The process as set forth in claim 1 in which said saccharide is fructose and said hydrogenated saccharide is a mixture of sorbitol and mannitol.

13. The process as set forth in claim 1 in which said saccharide is mannose and said hydrogenated saccharide is mannitol.

* * * * *